(12) United States Patent
Wachs

(10) Patent No.: US 6,683,221 B1
(45) Date of Patent: *Jan. 27, 2004

(54) PRODUCTION OF FORMALDEHYDE FROM $CH_4$ AND $H_2S$

(75) Inventor: Israel E. Wachs, Bridgewater, NJ (US)

(73) Assignee: Lehigh University, Bethlehem, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/937,225

(22) PCT Filed: Mar. 24, 2000

(86) PCT No.: PCT/US00/07826

§ 371 (c)(1),
(2), (4) Date: Feb. 1, 2002

(87) PCT Pub. No.: WO00/56692

PCT Pub. Date: Sep. 28, 2000

Related U.S. Application Data

(60) Provisional application No. 60/126,010, filed on Mar. 24, 1999.

(51) Int. Cl.[7] .......................... C07C 45/28; C07C 45/33
(52) U.S. Cl. .................. 568/475; 568/482; 568/493
(58) Field of Search ................................ 568/482, 493, 568/475

(56) References Cited

U.S. PATENT DOCUMENTS

| 4,544,649 A | 10/1985 | Wachs et al. ................ 502/350 |
| 5,969,191 A | 10/1999 | Wachs ......................... 568/493 |
| 6,028,228 A | * 2/2000 | Wachs |
| 6,084,135 A | * 7/2000 | Wachs |
| 6,410,793 B1 | 6/2002 | Wachs ........................ 568/21 |

FOREIGN PATENT DOCUMENTS

| WO | 86/06063 | 10/1986 |

* cited by examiner

*Primary Examiner*—Johann Richter
*Assistant Examiner*—Sikarl A. Witherspoon
(74) *Attorney, Agent, or Firm*—Banner & Witcoff, Ltd.

(57) ABSTRACT

A method wherein a sour natural gas stream can be treated to produce primarily carbon monoxide from methane, and the carbon monoxide and hydrogensulfide are reacted to produce methyl mercaptans, (primarily methanethiol ($CH_3SH$) and a small amount of dimethyl sulfide ($CH_3SCH_3$)). The methyl mercaptans preferably are passed in contact with a catalyst comprising a supported metal oxide or a bulk metal oxide in the presence of an oxidizing agent and for a time sufficient to convert at least a portion of the methyl mercaptan to formaldehyde ($CH_2O$), and sulfur dioxide ($SO_2$).

15 Claims, 2 Drawing Sheets

PRODUCTION OF FORMALDEHYDE FROM CH$_4$ AND H$_2$S

This application is a 35 U.S.C. 371 National Phase application of PCT/US00/07826 filed on Mar. 24, 2000, which claims the priority of U.S. Provisional Application No. 60/126,010 filed on Mar. 24, 1999.

BACKGROUND OF THE INVENTION

1. Field of the Invention

This invention broadly relates to a process for producing useful chemicals, and especially formaldehyde, from methane (CH$_4$) and hydrogen sulfide (H$_2$S), and especially from a gas stream containing a mixture of CH$_4$ and H$_2$S. More particularly, this invention provides a method wherein hydrogen sulfide, generally separated from a gas stream containing methane and hydrogen sulfide, is combined with a carbon oxide, wherein the carbon oxide is selected from carbon monoxide (CO), carbon dioxide (CO$_2$) and mixtures thereof, and the combined gas stream is passed in contact with a catalyst comprising a supported metal oxide of a metal selected from the group consisting of vanadium (V), niobium (Nb), molybdenum (Mo), chromium (Cr), rhenium (Re), titanium (Ti), tungsten (W), manganese (Mn), tantalum (Ta) and mixtures thereof to convert said carbon oxide and hydrogen sulfide mixture to methyl mercaptans, (methanethiol(CH$_3$SH) and dimethyl sulfide (CH$_3$SCH$_3$)). The methyl mercaptans can be used as a starting material for making additional products and preferably are then passed in contact with a catalyst comprising certain supported metal oxides or certain bulk metal oxides in the presence of an oxidizing agent and for a time sufficient to convert at least a portion of the methyl mercaptans to formaldehyde (CH$_2$O) and sulfur dioxide (SO$_2$). The carbon oxide used to react with the hydrogen sulfide is produced by the partial oxidation of methane in the presence of oxygen over a metal partial oxidation catalyst that promotes the partial oxidation of methane to carbon oxides, preferably CO, and hydrogen (H$_2$).

2. Description of Related Art

Natural gas recovered from geological formations often contains hydrogen sulfide as an undesired impurity in concentrations of 10–30%. The hydrogen sulfide is typically separated from the methane and often is converted to elemental sulfur via the Claus Process. In the Claus Process, a first portion of the separated hydrogen sulfide is converted (oxidized) to sulfur dioxide (SO$_2$) and the remaining portion of the hydrogen sulfide is reacted with the sulfur dioxide in the presence of a suitable catalyst to produce water and elemental sulfur. The so-produced sulfur represents a low value-added, commodity product; while the de-sulfurized methane typically is distributed for industrial and personal uses, such as for home heating. An alternative way for producing and using the hydrogen sulfide would significantly improve the economies of sour natural gas recovery and processing.

Ratcliffe et al., U.S. Pat. Nos. 4,570,020 and 4,668,825 describe catalytic processes for producing methanthiol (CH$_3$SH) from a gaseous feed comprising a mixture of carbon monoxide (CO) and hydrogen sulfide (H$_2$S). According to the '020 patent, the gaseous mixture is contacted, at a temperature of at least about 225° C. with a catalyst comprising a metal oxide of a metal selected from the group consisting of vanadium (V), niobium (Nb), and tantalum (Ta) and mixtures thereof supported as an oxide layer on titania. In the '825 patent, the gaseous mixture is contacted with a rutile titania catalyst under similar conditions. The methanethiol is disclosed as being useful as an odorant or tracer for natural gas and as a raw material for making methionine, fungicides and jet fuel additives.

The art has also identified methyl mercaptans, such as methanethiol (CH$_3$SH) and dimethyl sulfide (CH$_3$SCH$_3$), as hazardous pollutants, and has suggested a variety of ways for their destruction. Noncatalytic gas phase oxidation of such reduced sulfur compounds has been shown to produce primarily sulfur oxide and carbon oxide products. A. Turk et al., *Envir. Sci. Technol* 23:1242–1245 (1989). Investigators have observed that oxidation in the presence of single crystal metal surfaces (Mo, Ni, Fe, Cu) results in the formation of methane and ethane, nonselective decomposition to atomic carbon, gaseous hydrogen and the deposition of atomic sulfur on the metal surface via a stoichiometric reaction (See Wiegand et al., *Surface Science,* 279(1992): 105–112). Oxidation of higher mercaptans, e.g., propanethiol on oxygen-covered single crystal metal surfaces (Rh), produced acetone via a stoichiometric reaction at low selectivity and accompanied by sulfur deposition on the metal surface (See Bol et al., *J. Am. Chem. Soc.,* 117(1995): 5351–5258). The deposition of sulfur on the metal surface obviously precludes continuous operation.

The art also has disclosed using catalysts comprising a two-dimensional metal oxide overlayer on titania and silica supports, e.g., vanadia on titania, for catalytically reducing NO$_x$ by ammonia to N$_2$ and H$_2$O in the presence of sulfur oxides. Bosch et al., *Catal. Today* 2:369 et seq. (1988). Thus, such catalysts are known to be resistant to poisoning by sulfur oxides. It also is known that such catalysts, as well as certain bulk metal oxides catalysts, can be used to oxidize methanol to formaldehyde selectively. Busca et al, *J. Phys. Chem.* 91:5263 et seq. (1987).

Applicant discovered that supported metal oxide catalysts, such as vanadia on titania, can be used to oxidize methyl mercaptans, such as methanethiol (CH$_3$SH) and dimethyl sulfide (CH$_3$SCH$_3$), selectively to formaldehyde in a continuous, heterogenous catalytic process without being poisoned by the reduced sulfur. On the basis of that discovery, applicant now has envisioned the present novel process for converting methane, particularly methane in a sour natural gas stream, to formaldehyde.

BRIEF DESCRIPTION OF THE INVENTION

Figure 1:
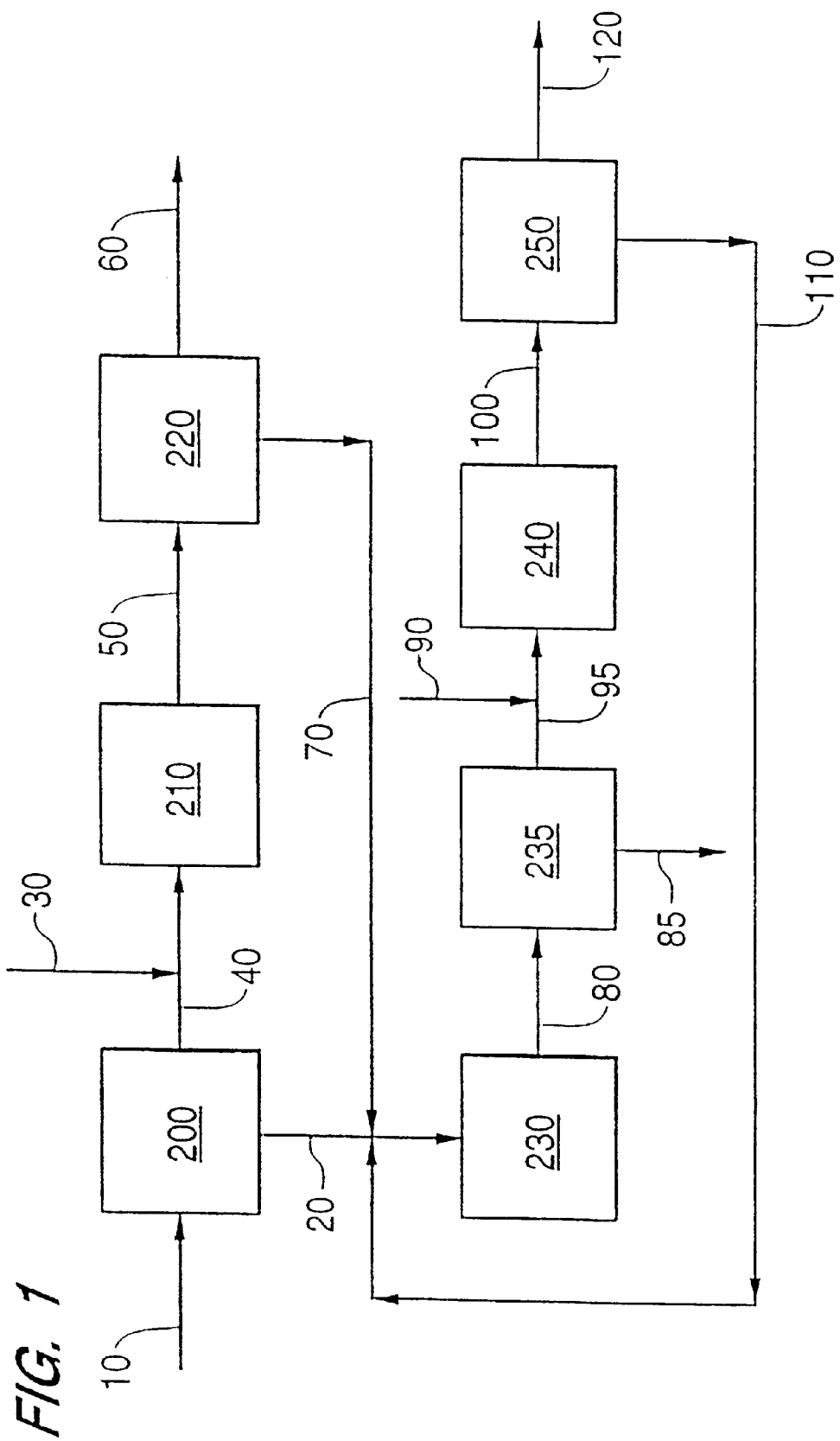
FIG. 1 is a schematic drawing of a preferred embodiment of the process of the present invention.
Figure 2:
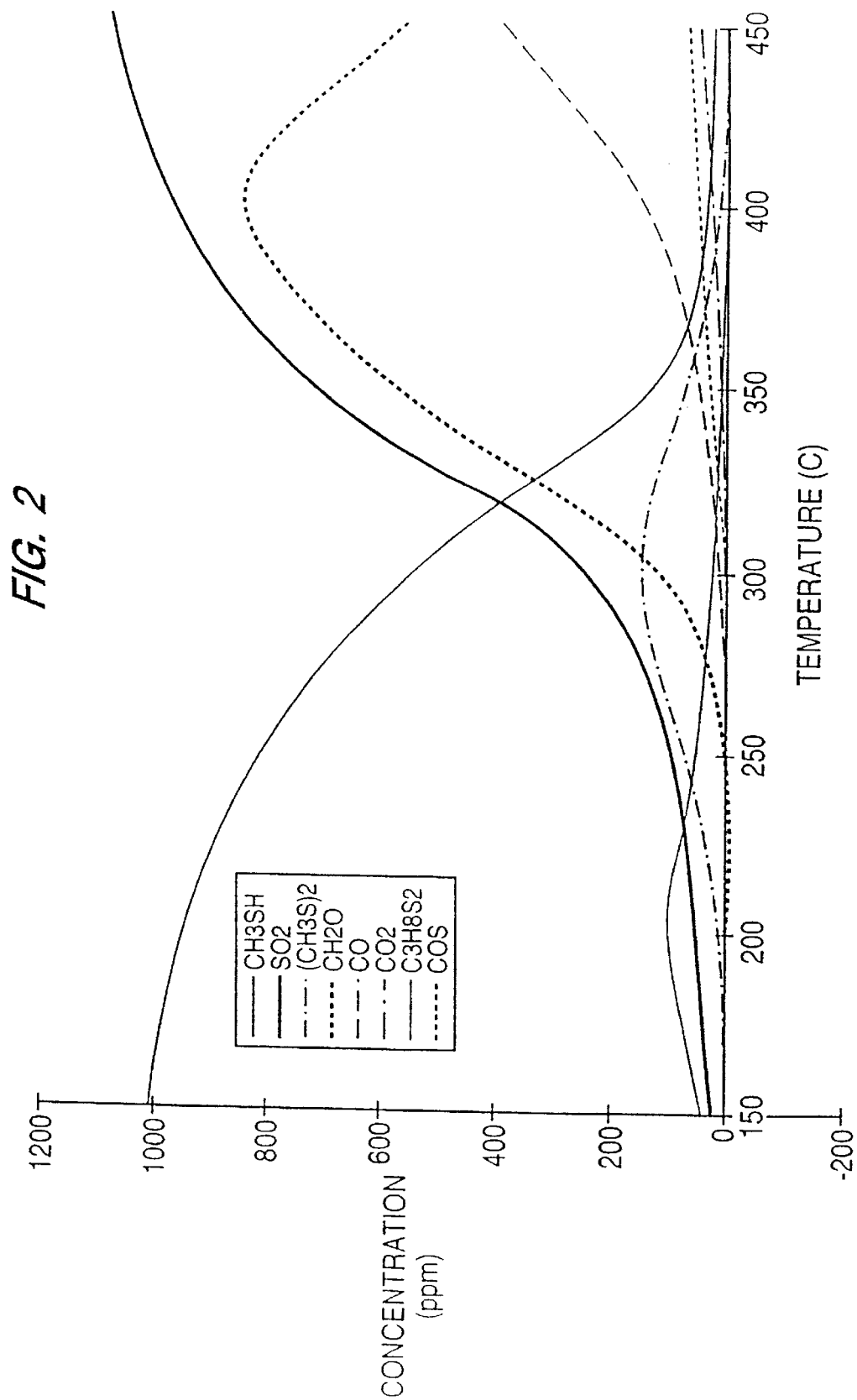
FIG. 2 illustrates the distribution of products produced by oxidizing methanethiol over a vanadia on titania catalyst containing about 1% by weight vanadia over the temperature range of 150° to 450° C. Maximum selectivity for the conversion of methanethiol to formaldehyde was observed at a temperature of about 400° C. Starting at about 300° C., there was a significant conversion of methanethiol to formaldehyde.

The present invention provides a process for facilitating the production of formaldehyde from a gas stream containing methane (CH$_4$) and is particularly useful for processing a sour natural gas stream containing a mixture of methane (CH$_4$) and hydrogen sulfide (H$_2$S) into formaldehyde and possibly other chemical products.

More particularly, this invention provides a method wherein methane is partially oxidized with oxygen over a well-known metal partial oxidation catalyst to carbon oxides, principally carbon monoxide, and hydrogen. The carbon oxides, recovered separate from the hydrogen and any unreated methane, is then combined with hydrogen sulfide and the combined gas stream is passed in contact with a catalyst comprising a supported metal oxide of a metal selected from the group consisting of vanadium (V), niobium (Nb), molybdenum (Mo), chromium (Cr), rhenium (Re), titanium (Ti), tungsten (W), manganese (Mn), tantalum (Ta) and mixtures thereof to convert said carbon oxides and hydrogen sulfide to methyl mercaptans, including methanethiol ($CH_3SH$) and dimethyl sulfide ($CH_3SCH_3$), which can be used as a raw material for the synthesis of other chemical products.

Preferably, the methyl mercaptans are passed thereafter into contact with a catalyst comprising certain supported metal oxides or certain bulk metal oxides in the presence of an oxidizing agent and for a time sufficient to convert at least a portion of the methyl mercaptans to formaldehyde ($CH_2O$) and sulfur dioxide ($SO_2$) and the formaldehyde is recovered separate from the sulfur dioxide. The sulfur dioxide can thereafter be converted to sulfuric acid.

In one preferred embodiment, a sour natural gas stream containing a mixture of methane ($CH_4$) and hydrogen sulfide ($H_2S$) first is treated to separate methane from the hydrogen sulfide, the methane is then partially oxidized to carbon oxides over a metal partial oxidation catalyst, while at least a portion of the so-separated hydrogen sulfide is reacted with the carbon oxides, recovered separately from the hydrogen produced during the partial oxidation of methane, to produce the methyl mercaptan.

DETAILED DESCRIPTION OF THE INVENTION

As noted, the present invention is directed to an alternative method for producing formaldehyde from a methane-containing gas stream, and especially from a sour natural gas stream containing a mixture of methane ($CH_4$) and hydrogen sulfide ($H_2S$). A key feature of the process is the selective conversion of carbon oxide, wherein the carbon oxide is selected from carbon monoxide (CO), carbon dioxide ($CO_2$) and mixtures thereof, which is produced from the partial oxidation of methane to hydrogen and carbon oxides, primarily carbon monoxide, first to methyl mercaptans, such as methanethiol ($CH_3SH$) and dimethylsulfide ($CH_3SCH_3$) (following combination of the carbon oxide with hydrogen sulfide ($H_2S$), such as may be recovered from a sour natural gas stream), and then to an additional chemical product, especially formaldehyde and sulfur dioxide.

Thus, in one important aspect, the process of the present invention involves flowing a gaseous stream containing carbon oxides and hydrogen sulfide ($H_2S$) in contact with a catalyst comprising a metal oxide of a metal selected from the group consisting of vanadium (V), niobium (Nb), molybdenum (Mo), chromium (Cr), rhenium (Re), titanium (Ti), tungsten (W), manganese (Mn), tantalum (Ta) and mixtures thereof supported, for example, on titania, zirconia, ceria, niobia, tin oxide or their mixture, preferably titania. As a general rule, the support and the supported metal should not be the same. The gaseous mixture is contacted with the metal oxide catalyst at a temperature of at least about 225° C. for a time sufficient to convert at least a portion of the carbon oxide and $H_2S$ to methyl mercaptan, primarily methanethiol. The gaseous stream containing the methyl mercaptan can then be used as a feedstock for applications where methyl mercaptans are used. For example, in a preferred embodiment of this invention, the methyl mercaptan can thereafter be contacted with a supported metal oxide or bulk metal oxide catalyst, under oxidizing conditions and for a time sufficient to convert at least a portion of the methyl mercaptan to formaldehyde and sulfur dioxide. The formaldehyde then can be recovered as a product separate from the gas stream.

In carrying out this aspect of the process of the present invention, the metal oxide overlayer of the supported metal oxide used in the process of converting methyl mercaptan to formaldehyde is typically based on a metal selected from the group consisting of titanium (Ti), zirconium (Zr), molybdenum (Mo), rhenium (Re), vanadium (V), chromium (Cr), tungsten (W), manganese (Mn), niobium (Nb), tantalum (Ta) and mixtures thereof and the support generally is selected from titania, silica, zirconia, alumina, ceria, magnesia, niobia, lanthanum oxide, tin oxide and mixtures thereof. Generally, a support of titania, zirconia, ceria, niobia or their mixture is preferred. As a general rule, titanium (Ti), zirconium (Zr), niobium (Nb), tantalum (Ta) and tungsten (W) should not be used as the sole catalytic species with a silica support, nor should the support and the supported metal be the same. In an alternative embodiment of the present invention, the optional step of the process, involving the conversion of methyl mercaptan to formaldehyde, also can be carried out using a bulk metal oxide catalyst wherein the bulk metal oxides, and especially bulk mixed metal oxides, are based on molybdates (Mo), chromates (Cr), vanadates (V), rhenates (Re), titanates (Ti), niobates (Nb), tungstates (W) and mixtures thereof. Catalysts based on molybdenum, chromium and vanadium are preferred.

The supported metal oxide and bulk metal oxide catalyst compositions useful for practicing the present invention are known in the prior art.

In a preferred embodiment, a supported metal oxide catalyst is used in both the reaction of carbon oxides with hydrogen sulfide and in the step of converting methyl mercaptan to formaldehyde and is preferably based on vanadium (V) oxide supported on titania. For the supported metal oxide catalyst used in the mercaptan to formaldehyde step, the vanadium oxide may preferably be used in mixture with an oxide of one of molybdenum (Mo), tungsten (W), chromium (Cr), rhenium (Re), niobium (Nb), tantalum (Ta) and manganese (Mn), supported on titania or silica. In the case of a vanadia on silica catalyst, an adjuvant selected from the group consisting of titanium, zirconium, cerium, tin, niobium and tantalum, should be present to enhance catalytic activity. As noted above, vanadia on titania is particularly preferred as a metal oxide supported catalyst in both of these steps according to this aspect of the inventive process.

In accordance with the present invention, and with reference to FIG. 1, one embodiment of the present invention is described. As noted, one suitable source for both the methane and hydrogen sulfide used in carrying out the process of the invention can be a sour natural gas. In the FIG. 1 process, this sour natural gas stream 10 is delivered to a separation zone 200 from which separate streams of hydrogen sulfide 20 and methane 40 are produced. Methods for separating the hydrogen sulfide from the sour natural gas containing methane and hydrogen sulfide are well known and have long been practiced in the art. Thus, such methods need no further description. Any of the widely available methods can be used to produce the separate gas streams of methane 40 and hydrogen sulfide 20, used to practice this embodiment of the present invention.

The so-separated methane 40 then is reacted in the presence of an oxidizing agent, such as molecular oxygen, introduced through stream 30, into partial oxidation reaction zone 210 containing a well-known metal partial oxidation catalyst to partially oxidize the methane at a temperature in the range of 300° to 1300° C., and generally in the range of 700° to 1000° C., primarily to carbon monoxide and hydrogen. Suitable, known supported metal catalysts include cobalt, nickel, iron, platinum, paladium, rhodium, and rehnium, often supported on alumina, mixed oxides of lanthana/zirconia and yttria/zirconia, and cobalt-rare earth mixed oxides. A small amount of steam also may be delivered to reaction zone 210 to suppress the formation of coke and minimize the production of carbon dioxide. Reactor 210 preferably is operated in a way to ensure that there is no residual oxidizing agent in stream 50. Ways for conducting the partial oxidation of methane to hydrogen and carbon oxides are well-known to those skilled in the art.

The carbon oxides produced via the partial oxidation of methane are used directly to produce a methyl mercaptan stream, which mercaptan can be used for further chemical synthesis, particularly for the preparation of additional formaldehyde.

In this regard, the carbon oxide-containing product gas stream in line 50, also containing hydrogen and unreacted methane, is passed to a separation zone 220 where by-product hydrogen and any unreacted methane are recovered in stream 60 separate from a carbon oxide-enriched stream in line 70. The necessary separation can be performed by chemical absorption (e.g., treated with N-methyl diethanolamine which can recover a concentrated carbon monoxide stream separate from and by-product carbon dioxide, or by fractional condensation). Again, methods for separating the carbon oxides from the residual gas and for concentrating the carbon monoxide portion of the gas are well known and need no further description. Any of the widely available methods can be used to produce the separate streams of residual gas 60 and carbon oxide 70. The unreacted methane in stream 60 can be recovered and recycled (not shown) to the partial oxidation reactor.

In accordance with this embodiment of the invention, the carbon oxide gas stream 70 is combined with hydrogen sulfide ($H_2S$) gas provided in line 20 for reaction in catalytic reaction zone 230. In this embodiment, the hydrogen sulfide is produced by separating it from a sour natural gas. Obviously, any source of hydrogen sulfide can be used in the broad practice of the present invention. In reactor 230, the combined $H_2S$ and carbon oxide reactants are passed in contact, at a temperature of at least 225° C., with a catalyst, preferably comprising a titania supported metal oxide of a metal selected from the group consisting of vanadium (V), niobium (Nb), molybdenum (Mo), chromium (Cr), rhenium (Re), titanium (Ti), tungsten (W), manganese (Mn), tantalum (Ta) and mixtures thereof. Alternatively, the support could be selected from zirconia, ceria, tin oxide, niobia or their mixture with each other and with titania, provided that the support and the supported metal generally should not be the same. The contacting is conducted for a time sufficient to convert the mixture of carbon oxides and hydrogen sulfide to methyl mercaptans, (e.g., methanethiol ($CH_3SH$) and dimethyl sulfide ($CH_3SCH_3$)).

As described in U.S. Pat. No. 4,570,020, the onset of methanethiol production from a mixed gas feed of CO and $H_2S$ over a titania-based catalyst starts to occur at a temperature of about 225° C., is more pronounced at about 250° C., and reaches a peak (under the particular reaction conditions and feed mixture reported in that patent) or optimum at a temperature of about 325° C. However, methanethiol tends to encounter thermal instability at 350° C. Therefore, if the reaction temperature approaches and/or exceeds this temperature, the prior art suggests that one take provisions to rapidly quench the so-formed methanethiol down to a temperature below about 350° C. in order to prevent thermal decomposition thereof.

In general, the ratio of $H_2S$ to CO in the gaseous feed used in this step of the process of this invention will typically range from about 1/4 to 40/1 and more preferably from about 1/2 to 4/1 on a mole basis. As reported in U.S. Pat. No. 4,570,020, it was found experimentally that a 1/1 ratio appears to be the optimum for maximum conversion of the feed. The reaction temperature will generally range from about 225° to 450° C., preferably 250° to 400° C. and still more preferably from about 300° to 400° C.

However, as previously stated, the prior art suggests that exceeding a reaction temperature of 350° C. may necessitate a quenching of the methyl mercaptan product recovered from this step in order to reduce or avoid its thermal decomposition. With regard to the space velocity of the feed, it is understood that longer contact times will result in a greater amount of desired product. However, this may be offset by decomposition of methyl mercaptan product in contact with the catalyst. In general, to account for competing reactions it is anticipated that the space velocity often will be maintained below about 4800 V/V/hr.

The reactor 230 is preferably operated at a superatmospheric pressure. An operating pressure up to 50 atmospheres is expected to be suitable, e.g., a pressure of 30–50 atmospheres. Because the reaction of CO and $H_2S$ is preferably conducted in the gas phase, the total reactor pressure normally should not result in a partial pressure of $H_2S$ that would cause the $H_2S$ to condense. Accordingly, unless it is desired in a specific circumstance that the reaction occur in the presence of both gaseous and liquid phases, the reactor conditions should be maintained to avoid $H_2S$ condensation.

The methyl mercaptan stream can be recovered or can be used as a raw material for the synthesis of a variety of chemical products. In the present embodiment, the methyl mercaptan-containing stream 80 issuing from reaction zone 230 is passed to separation zone 235 for separation of the methyl mercaptan product 95 from any unreacted hydrogen sulfide, by-product hydrogen, COS, and possibly unreacted carbon oxides (and any methane not previously removed) via line 85. As will be recognized by those skilled in the art, a variety of separation processes can be used to remove any undesired constituents from the desired mercaptan product, including absorption, adsorption and fractional condensation techniques, prior to reaction zone 240.

Methyl mercaptan product 95 then contacts, in the gas phase, a supported metal oxide or a bulk metal oxide catalyst in reaction zone 240 under oxidizing conditions at a temperature in the range of 200° to 700° C., preferably in the range of 300° to 600° C., and most often in the range of 325° to 500° C. The operating pressure for the catalytic reactor 240 is not critical with operation at atmospheric pressure being generally suitable.

Air or enriched oxygen is added via stream 90 to the mercaptan product stream to establish oxidizing conditions in the reaction zone 240. The selective oxidation of the methyl mercaptan produces formaldehyde and sulfur dioxide, which exits reaction zone 240 in stream 100. As noted, the oxidizing agent used in the selective methyl mercaptan oxidation can usually be oxygen or air. The contacting of the methyl mercaptan with the supported metal oxide catalyst or bulk metal oxide catalyst under an oxidizing atmosphere, e.g., in the presence of oxygen, and at an appropriate temperature, causes a selective conversion of the methyl mercaptan to formaldehyde. Although not required, reactor 240 preferably can be operated in a way to ensure that there is no residual oxidizing agent in stream 100 although it is adequate to remove excess oxygen in separation zone 250.

Formaldehyde is the intended product of this preferred embodiment of the present process and it can be recovered from the gaseous reaction product 100 in separation zone 250 using anyone of a number of ways known to those skilled in the art.

In particular, as will be recognized by those skilled in the art, the gases 50 and 100 leaving the reaction zones 210 and 240, respectively, may contain unreacted starting products, including any inert gases that may have been added. The principal products formed by the partial oxidation of methane are carbon oxides; while the principal by-products formed in the partial oxidation of methyl mercaptans include carbon oxides (mainly carbon monoxide, which may be accompanied by a small amount of carbon dioxide), and sulfur, dioxide. COS will likely be a sizable by-product of the $H_2S$ and CO reaction; but only a minor product of the partial oxidation of methyl mercaptan.

The formaldehyde-containing reaction mixtures leaving the methyl mercaptan partial oxidation reaction zone 240 is generally subject to further processing in separation zone 250 in a conventional manner. For example, the formaldehyde product can be separated in a washer, or by indirect cooling, or also by fractional cooling. For example, the washing can be performed with water, in which case a multi-stage washer can be used. Aqueous formaldehyde solution 120 can be obtained in this manner. From solution 120, a commercial formaldehyde solution can be prepared by distillation for subsequent technical use. The formaldehyde also can be condensed out of the reaction gas together with the water that has formed. In this manner, concentrated formaldehyde solutions in common commercial form may be obtained. Other ways for isolating the formaldehyde product from the product gases will be apparent to those skilled in this art.

Sulfur dioxide formed in reaction zone 240 also can be removed in separation zone 250, or alternatively can be removed from stream 110 before recycling. Methods for removing $SO_2$ from these streams will be recognized by those skilled in the art, again absorption, adsorption and fractional condensations techniques should be suitable. The $SO_2$ can be oxidized to sulfuric acid. Residual gas 110 from separation zone 250, possibly containing carbon oxides may be recycled to the methyl mercaptan production step in reaction zone 230. Separation of carbon oxides from the $SO_2$ would permit recycle of the carbon oxides. The Citrex process for preferentially absorbing $SO_2$ is one option. The reactor effluent gas remaining after separation of the formaldehyde and the other constituents could then be recycled.

The catalysts useful in promoting the reaction of carbon monoxide and hydrogen sulfide to methyl mercaptans comprise a support of titania, zirconia, ceria, tin oxide, niobia or their mixture whose surface has been modified with an oxide of a metal selected from vanadium (V), niobium (Nb), molybdenum (Mo), chromium (Cr), rhenium (Re), titanium (Ti), tungsten (W), manganese (Mn), tantalum (Ta) and mixtures thereof. That is, the surface of the titania, zirconia, ceria, niobia or their mixture has been modified by an oxide layer of vanadium (V), niobium (Nb), molybdenum (No), chromium (Cr), rhenium (Re), titanium (Ti), tungsten (W), manganese (Mn), tantalum (Ta) or a mixture thereof in an amount such that the catalyst exhibits properties different from titania whose surface has not been modified and different from bulk oxides of vanadium, niobium, molybdenum, chromium, rhenium, tungsten, tantalum or a mixture thereof. As a general rule, the support and the supported metal should not be the same. Consequently, the metal oxide loading on the support should be sufficient to modify the titania, zirconia, ceria, niobia, tin oxide or their mixture surface, but preferably is not enough to result in a catalyst exhibiting properties of the bulk oxides of vanadium, niobium, molybdenum, chromium, rhenium, titanium, tantalum or a mixture thereof. Thus, at least a portion of, and preferably at least about 30 wt. % of, the metal oxide will be in a non-crystalline form. This will be accomplished if the metal oxide loading on the metal oxide support broadly ranges between about 0.5 to 30 wt. % of the total catalyst weight.

The metal oxide of the supported metal oxide catalyst in the reaction zone 240 also is accommodated in the support primarily as a two-dimensional metal oxide overlayer (possibly a monolayer), with the oxide having a noncrystalline form. Supported metal oxide catalysts useful in this reaction zone generally comprise a metal oxide substrate, such as titania, silica, zirconia, alumina, niobia, ceria, magnesia, lanthanum oxide, tin oxide and mixtures thereof, whose surface has been modified with a layer of an oxide of a metal or a mixture of metals as identified above (e.g., preferably vanadium, and mixtures containing vanadium) in an amount such that the catalyst exhibits properties different from the metal oxide substrate whose surface has not been modified. These catalysts also behave differently from bulk metal oxides of the metal oxide overlayer (e.g., bulk oxides of vanadium, and its mixtures). Consequently, in this embodiment of the invention, the metal oxide loading on the metal oxide support or substrate, e.g., titania, must be sufficient to modify the metal oxide surface, but not enough to result in a catalyst exhibiting properties of the bulk oxides of the metal oxide overlayer, e.g., a bulk oxide of vanadia. Thus, at least a portion of and preferably at least about 25 wt % of the metal oxide coating will be in a non-crystalline form. This will be accomplished if the metal oxide loading on the metal oxide support or substrate broadly ranges between about 0.5 to 35 wt % of the total catalyst weight.

A preferred metal oxide support for use in both steps 230 and 240 of this embodiment of the process is titania (titanium dioxide) which can be employed in the anatase or rutile form. For example at least about 25 wt % (and generally from about 50 to about 100 wt %) of the titanium dioxide ($TiO_2$) can be in the anatase form. As recognized by those skilled in the catalytic art, the titania support material needs to be judiciously evaluated since certain grades may have impurities that interfere with the catalytic activity. Normally, with recognition of the previous caveat, the titanium dioxide may be prepared by any conventional technique. The titanium dioxide used in the catalysts of this aspect of the invention may be composed of substantially porous particles of a diameter of from about 0.4 to about 0.7 micron and preferably has a specific surface area of at least about 1 $m^2/g$.

The metal oxide supported catalysts used in any of the steps of the process of this invention may be prepared by impregnation techniques well-known in the art, such as incipient wetness, grafting, equilibrium adsorption, vapor deposition, thermal spreading, etc. When using an incipient wetness impregnation technique, an aqueous or non-aqueous solution containing a metal oxide precursor compound(s) is contacted with the metal oxide support or substrate material, e.g., silica or titania, for a time sufficient to deposit a metal oxide precursor material onto the support such as by selective adsorption or alternatively, excess solvent may be evaporated leaving behind the precursor compound or salt. If an incipient wetness impregnation technique is used to prepare a catalyst of this invention, the metal oxide precursor (e.g., salt) solution used may be aqueous or organic, the only requirement being that an adequate amount of a precursor compound for the selected metal oxide be soluble in the solvent used in preparing this solution. Other impregnation techniques, such as vapor deposition and thermal spreading, do not require use of a solvent as does incipient wetness, and may be desirable in some circumstances to avoid the problem of volatile organic carbon (VOC) emissions.

For example, one way to disperse vanadium oxide, tungsten oxide or a combination of the two oxides onto a titania metal oxide support or substrate is to impregnate titania spheres or powder (spheres or powder are used as representative examples of shapes of titania) with a solution containing a vanadium or a tungsten compound. When impregnating a substrate with both oxides, the tungsten and vanadium are introduced in a stepwise manner, tungsten first, followed by vanadium, with appropriate intermediate drying and calcining steps. Each solution may be an aqueous solution, one using an organic solvent or a mixture of the two. Generally, an aqueous solution is preferred. Criteria used to choose the vanadium and tungsten compounds include whether the compounds are soluble in the desired solvent and whether the compounds decompose at an acceptable rate at a high, calcination temperature to give the appropriate metal oxide. Illustrative of suitable compounds of vanadium and tungsten are the halides of vanadium and tungsten, oxyacids, oxyacid salts and oxysalts of vanadium and tungsten. Specific examples are tungsten dibromide, tungsten pentabromide, tungsten tetrachloride, tungsten dioxydichloride, tungstic acid, ammonium meta-tungstate, vanadium tribromide, vanadium dichloride, vanadium trichloride, vanadium oxychloride, vanadium oxydichloride, vanadic acid, vanadyl sulfate, vanadium alkoxides, vanadium oxalate (which may be formed in situ by reaction of $V_2O_5$, and an aqueous solution of oxalic acid), and ammonium meta-vanadate. Suitable metal oxide precursor compounds for the other metal species suitable for making the supported metal oxide catalysts of this invention are well recognized by those skilled in the catalysis art.

The impregnation of the metal oxide support or substrate, e.g., titania or silica support spheres or powder, with the metal oxide precursor compound solution may be carried out, as noted above, in ways well known in the art using either wet or dry impregnation techniques. One convenient method is to place the metal oxide support or substrate, e.g., titania or silica particles, into a rotary evaporator which is equipped with a steam jacket. An impregnating solution of a precursor compound which contains an amount of the desired metal to be included in the finished catalyst (as the metal) is added to the support particles and the mixture is cold rolled (no steam) for a time from about 10 to 60 minutes sufficient to impregnate the support with the precursor compound solution. Next, steam is introduced and the solvent is evaporated from the impregnated solution. This usually takes from about 1 to about 4 hours. The impregnated support will normally be dried at temperatures ranging from about 50°–300° C. to remove excess solvent.

Water soluble precursor compounds are generally preferred for industrial applications because of the environmental concern about VOC emissions. Nonetheless, when using an organic solvent, initial heating may be done in a nitrogen atmosphere to remove any flammable solvent. Finally, the support particles are removed from the rotary evaporator and calcined in a suitable oxidizing atmosphere such as air, oxygen, etc. at a temperature of about 150° to 800° C., and more usually from 400°–600° C., preferably for about 1 to about 3 hours, sufficient to decompose the precursor compound to the corresponding metal oxide. In other cases, as recognized by those skilled in the art, calcining conditions need to be adjusted to avoid undesirably reducing surface area.

Because some precursor compounds are air/moisture sensitive, they are commonly prepared under a nitrogen atmosphere as is recognized by those skilled in this art. The time required to calcine the composite will, of course, depend on the temperature and in general will range from about 0.5–7 hours. Calcination at 450° C. for about 2 hours has proven to be suitable for 1% vanadia on titania catalyst. The precise time and temperature for calcination depends on the particular metal oxide overlayer and should be selected to avoid adversely affecting the metal oxide support, e.g., in the case of a titania metal oxide support, to avoid substantial crystal phase transformation of the anatase into another crystalline form, e.g., rutile, and degradation of extended surface areas. Selection of a suitable combination of time and temperature is a matter of routine testing to those skilled in the art.

Reducing atmospheres may also be used to decompose the transition metal oxide precursors. To avoid potential safety concerns, the resulting composite should be calcined to convert the reduced metal component to the oxide form. If the support is to be provided with an overlayer of a combination of metal oxides, e.g., if an overlayer containing both vanadium and tungsten oxide is desired, then the metal oxide precursor compounds may be impregnated on the metal oxide support simultaneously, but preferably are impregnated sequentially as previously noted.

The metal oxide supported catalysts used in the process of this invention will generally have surface metal oxide loadings of from about 0.5 to 35 wt. % metal oxide based on the total active catalyst composition, preferably from about 1 to 20 wt. %, more usually from about 1–15 wt. %, and most preferably 1–10 wt. % based on the total active catalyst composition.

While titania, silica, zirconia, alumina, niobia, ceria, magnesia, lanthanum oxide and tin oxide are conveniently referred to as supports or substrates in the description of the preferred embodiment of the present invention, based to a large degree on the way the catalysts are prepared, it should be noted that they provide important roles as active catalytic components in the supported metal oxide catalyst. Combination supports may also be advantageous for use in catalysts suitable for practicing the methyl mercaptan to formaldehyde conversion step of the preferred embodiment of the invention. For example, substrates constituting a mixture of titania and zirconia or titania and silica can be used.

Further details on the preparation and structure of metal oxide supported catalysts useful in the practice of the present invention can be found in Jehng et al., *Applied Catalysis A,* 83, (1992) 179–200; Kim and Wachs, *Journal of Catalysis,* 142, 166–171; Jehng and Wachs, *Catalysis Today,* 16, (1993) 417–426; Kim and Wachs, *Journal of Catalysis,* 141, (1993) 419–429; Deo et al., *Applied Catalysis A,* 91, (1992) 27–42; Deo and Wachs, *Journal of Catalysis,* 146, (1994) 323–334; Deo and Wachs, *Journal of Catalysis,* 146, (1994) 335–345; Jehng et al., *J. Chem. Soc. Faraday Trans.,* 91(5), (1995) 953–961; Kim et al., *Journal of Catalysis,* 146, (1994) 268–277; Banares et al., *Journal of Catalysis,* 150, (1994) 407–420 Jehng and Wachs, *Catalyst Letters,* 13, (1992) 9–20; Sun et al., *Methane and Alkane Conversion Chemistry,* pp. 219–226 (1995); Herman et al., *Catalysis Today,* 37: 1–14 (1997) and Sun et al., *J. of Catalysis,* 165, 91–101 (1997), the disclosure of which are incorporated herein by reference.

Preferred supported metal oxide catalysts for the step of partial oxidation of methyl mercaptans to formaldehyde are those which are known to be suitable for converting methanol to formaldehyde. Particularly preferred are supported metal oxide catalysts comprising a vanadia overlayer on a titania support.

It often is desired that the metal oxide, such as titania, silica, zirconia, alumina niobia, magnesia, ceria, lanthanum oxide, tin oxide, and their mixtures, used as a catalyst support component in accordance with the present invention have a surface area in the range of about 5 to about 150 m$^2$/g and higher. These materials may be used in any configuration, shape or size which exposes their surface and any metal oxide layer dispersed thereon to the gaseous stream passed in contact therewith. For example, these oxide supports, such as titania can conveniently be employed in a particulate form or deposited (before or after impregnation with the metal oxide overlayer) on a monolithic carrier or onto ceramic rings or pellets. As particles, the support, such as titania, can be formed in the shape of pills, pellets, granules, rings, spheres and the like. Use of free particulates might be desirable when large catalyst volumes are needed or if the catalyst bed is operated in a fluidized state. A monolithic form or deposition of the active catalyst on an inert ceramic support might be preferred in applications where catalyst movement is to be avoided because of concerns about catalyst attrition and dusting, and a possible increase in pressure drop across a particulate bed. In a preferred approach, a metal oxide supported catalyst, such as a vanadia on titania catalyst, may be deposited on a ceramic carrier such as silicon carbide, silicon nitride, carborundum steatite, alumina and the like, provided in the shape of rings or pellets. Typically, the active catalyst will be applied to the inert ceramic support in an amount to provide 1 to 20% by weight of the supported catalyst.

As noted, the present invention also contemplates the use of bulk metal oxides as the catalyst for converting methyl mercaptan to formaldehyde in the preferred embodiment. Such bulk metal oxide catalysts generally constitute molybdates (Mo), chromates (Cr), vanadates (V), rhenates (Re), titanates (Ti), niobates (Nb), tungstates (W) and mixtures thereof. Such metal oxides also contain a wide variety of other metal species such as alkali metals (e.g., sodium (Na), lithium (Li), potassium (K) and cesium (Cs)), alklaine earth metals (e.g., calcium (Ca), barium (Ba), and magnesium (Mg)) and transition metals (e.g., copper (Cu), nickel (Ni), cobalt (Co), aluminum (Al), lead (Pb), bismuth (Bi), iron (Fe), zinc (Zn), cadmium (Cd), tellurium (Te), manganese (Mn)). Those skilled in the art recognize the wide variety of available bulk metal oxide catalysts. As a general rule, those bulk metal oxide catalysts known to be suitable for converting methanol to formaldehyde also may be suitable for the methyl mercaptan to formaldehyde conversion of the present invention.

Methods for making bulk metal oxide catalysts used in the present invention also are well known to those skilled in the art. In particular, the active catalyst can be prepared by physically blending the metal oxides, by coprecipitation from aqueous solutions containing soluble compounds of the catalyst components in the desired molar ratio or by any other technique which provides an intimate mixture of the metal oxide constituents. For example, an aqueous solution of a water-soluble molybdenum compound (ammonium heptamolybdate) is mixed with a water-soluble iron compound (ferric chloride) to cause coprecipitation of both molybdenum and iron, using procedures well known to those skilled in the art. The coprecipitate is washed, to eliminate the soluble salts formed during the coprecipitation reactions, filtered, dried and calcined to convert the metal constituents to their active iron molybdate (oxide) form. Those skilled in the art recognize a variety of water soluble metal compounds that can be used to prepare the active catalyst. Alternatively, oxides of the respective metals may be ground together and calcined. Additional details on bulk metal oxides and bulk metal oxide catalysis can be found in Arora et al., *Journals of Catalysis,* 159, (1996) 1–13, which is incorporated herein by reference.

Those skilled in the art recognize that there exists a wide range of compounds, generally used in admixture, suitable for preparing bulk metal oxide catalysts. The following is a representative, though not exhaustive, list of possible constituents: bulk vanadates such as $PbV_2O_6$, $NaVO_3$, $Na_3VO_4$, $BiVO_4$ and other Bi—V—O family members, $AlVO_4$, $FeVO_4$, $Mg_3(VO_4)_2$, $Mg_2V_2O_7$, $CeVO_4$, $Zn_3(VO_4)_2$, $CdV_2O_7$, $Zn_2V_2O_7$, $VOPO_4$ and other V—P—O family members, $KVO_3$, $Pb_2V_2O_7$, and $TlVO_4$; bulk molybdates such as $PbMoO_4$, $CaMoO_4$, $Bi_2Mo_2O_9$, $Bi_3(FeO_4)(MoO_4)_3$ and other Bi—Mo—O family members, $Na_2MoO_4$, $MnMoO_4$, $Gd_2(MoO_4)_3$, $MgMoO_4$, $CuMoO_4$, $CoMoO_4$, $Fe_2(MoO_4)_3$, $Te_2MoO_7$, $CoMoO_4$, $Al_2(MoO_4)_3$, $Cr_2(MoO_4)_3$, and $Na_2Mo_2O_7$; bulk niobates such as $YNbO_4$, $YbNbO_4$, $LiNbO_3$, $NaNbO_3$, $KNbO_3$, $AlNbO_4$, $K_8Nb_6O_{19}$, $BiNbO_4$, and other Bi—Nb—O family members, $SbNbO_4$, $NbOPO_4$, $CaNb_2O_6$, $K_4Nb_6O_{17}$, and $KCa_2Nb_3O_{10}$; bulk tungstates such as $Li_6WO_6$, $FeWO_4$, $CoWO_4$, $MnWO_4$, $NiWO_4$, $CuWO_4$, $CaWO_4$, $Cs_2WO_4$, $Na_2WO_4$, $B_aWO_4$, $Fe_2(WO_4)_3$, $Al_2(WO_4)_3$, $SrWO_4$, $K_2WO_4$, $Na_2W_2O_7$, $Li_2WO_4$, $CsLuW_2O_8$, $BiWO_4$, and other Bi—W—O family members; bulk chromates such as $Na_2CrO_4$, $Na_2Cr_2O_7$, $Na_2Cr_3O_{10}$, $Na_2Cr_4O_{13}$, $K_2CrO_4$, $K_2Cr_2O_7$, $K_2Cr_3O_{10}$, $K_2Cr_4O_{13}$, $Fe_2(CrO_4)_3$, $CaCrO_4$, $Cs_2CrO_4$, $BiCrO_4$ and other Bi—Cr—O family members; bulk rhenates such as $NaReO_4$, $Li_6ReO_4$, and $Mg(ReO_4)_2$; and bulk titanates such as $Na_2TiO_4$, $NaTiO_3$, $BaTiO_4$, $BaTiO_3$, and other Ba—Ti—O family members.

To achieve high selectivity in the conversion of methyl mercaptan to formaldehyde it is important to maintain the flow rate of methyl mercaptan per unit mass of catalyst in the range of $10^{-2}$ to $10^4$ cubic centimeters (STP) of methyl mercaptan per gram of active catalyst per minute (excluding inert ceramic components or other inert support material). Generally, higher reaction temperatures permit higher flow rates. Usually, the process can be operated at 0.1 to 100, cubic centimeters (STP) of methyl mercaptan per gram of catalyst per minute.

As used herein, the term "selectively" is intended to embrace the conversion of at least 1% of the methyl mercaptan, preferably at least 10% of the methyl mercaptan, more usually at least 50% of the methyl mercaptan and most preferably at least 70% of the methyl mercaptan which contacts the catalyst to formaldehyde. Selectivity, as that term is used herein, is determined by the percentage of formaldehyde in the mercaptan conversion products as a proportion of the carbon-containing mercaptan oxidation products.

The oxidation reaction of the methyl mercaptan to formaldehyde step is exothermic. As recognized by those skilled in the art a variety of reactor designs may be employed to accommodate the necessary mass and heat transfer processes for effective operation on a continuous basis. The reaction may be conducted at atmosphere pressure, and above or below atmospheric pressure.

EXAMPLES

To facilitate a more complete understanding of the invention, a number of Examples are provided below. The scope of the invention, however, is not limited to specific embodiments disclosed in these Examples, which are for purposes of illustration only. These examples illustrate that aspect of the invention relating to the partial oxidation of methyl mercaptans to formaldehyde.

Examples 1–13

Supported metal oxide catalysts were prepared as follows:

Example 1

Vanadia on Titania

A vanadia on titania metal oxide supported catalyst was prepared in accordance with the following procedure. The vanadia-titania catalyst was prepared by using $TiO_2$ (Degussa P25) as the support. The $TiO_2$ support (~10% rutile and ~90% anatase) possessed a surface area of ~55 $m^2/g$. It was calcined in air at 500° C. and cooled to room temperature before impregnation with the vanadium oxide precursor. The vanadium oxide overlayers on the $TiO_2$ support were prepared from vanadium triisopropoxide oxide (Alfa, 95–98% purity) by the incipient wetness impregnation method. The preparation was performed under a nitrogen environment and in nonaqueous solutions, since the alkoxide precursor is air and moisture sensitive. Solutions of known amounts of vanadium triisopropoxide oxide and propanol-2, corresponding to the incipient wetness impregnation volume and the final amount of vanadium required, were prepared in a glove box filled with nitrogen. The solutions of the vanadium precursor and propanol-2 were then thoroughly mixed with the titania support and dried at room temperature in the glove box for 24 hr. The impregnated samples were heated to 300° C. in flowing nitrogen and the final calcination was performed in $O_2$ (Linde, 99.9% pure) at 500° C. for 15 hours. The catalyst was then pelletized, crushed and sieved to obtain catalyst particles sizes between 100 to 200 $\mu$m.

Example 1A

Vanadia on Titania

Another vanadia on titania metal oxide supported catalyst was prepared using the general procedure of Preparation Example 1 except that the final calcination was conducted at 450° C. for 2 hours.

Example 2

Molybdenum Oxide on Titania

An aqueous solution of ammonium heptamolybdate $((NH_4)_6Mo_7O_{24}.4H_2O)$ (Alfa) was deposited onto $TiO_2$ (Degussa P25) as the support (~10% rutile and ~90% anatase) by the incipient wetness technique. As in Example 1, the support was calcined in air at 500° C. and cooled to room temperature before impregnation with the molybdenum oxide precursor. The support possessed a surface area of ~55 $m^2/g$. After impregnation, the wet samples were dried at room temperature for 16 hours, further dried at 110–120° C. for 16 hours and calcined at 450° C. for 12 hours. The catalyst was then pelletized, crushed and sieved to obtain catalyst particles sizes between 100 to 200 $\mu$m.

Example 3

Chromia on Titania

An aqueous solution of chromium nitrate $(Cr(NO_3)_3.9H_2O)$ (Allied Chemical Co.) was deposited onto $TiO_2$ (Degussa P25) as the support using the incipient wetness technique. As in the previous Examples, the $TiO_2$ support (~10% rutile and ~90% anatase) was calcined in air at 500° C. and cooled to room temperature before impregnation with the chromium precursor. The support possessed a surface area of ~55 $m^2/g$. After impregnation, the wet samples were dried at room temperature for 16 hours, further dried at 110–120° C. for 16 hours and calcined at 450° C. for 13 hours. The catalyst was then pelletized, crushed and sieved to obtain catalyst particles sizes between 100 to 200 $\mu$m.

Example 4

Rhenium Oxide on Titania

An aqueous solution of perrhenic acid $(HReO_4)$ (Aldrich) was deposited onto $TiO_2$ (Degussa P25) as the support using the incipient wetness technique. As before, the $TiO_2$ support (~10% rutile and ~90% anatase) was calcined in air at 500° C. and cooled to room temperature before impregnation with the rhenium oxide precursor. The support possessed a surface area of ~55 $m^2/g$. After impregnation, the wet samples were dried at room temperature for 16 hours, further dried at 110–120° C. for 16 hours and calcined at 450° C. for 13 hours. The catalyst was then pelletized, crushed and sieved to obtain catalyst particles sizes between 100 to 200 $\mu$m.

Example 5

Vanadia on Zirconia

A vanadium oxide overlayer was deposited onto a zirconium oxide $(ZrO_2)$ support (Degussa) having a surface area ~39 $m^2g^{-1}$ using an organic solution of vanadium triisopropoxide oxide (Alfa, 95–98% purity). In particular, the vanadium overlayer was prepared by the incipient wetness impregnation method using a solution of vanadium triisopropoxide oxide and propanol-2 in a glove box filled with nitrogen. The solutions of the vanadium precursor and propanol-2 were thoroughly mixed with the zirconia support and dried at room temperature for 16 hours, further dried at 110–120° C. for 16 hours and calcined at 450° C. for 16 hours. The catalyst was then pelletized, crushed and sieved to obtain catalyst particles sizes between 100 to 200 $\mu$m.

Example 6

Vanadia on Niobia

A vanadium oxide overlayer was deposited on a niobia $(Nb_2O_5)$ support (55 $m^2g^{-1}$) using vanadium triisopropoxide oxide (Alfa, 95–98% purity) and the incipient wetness technique. The niobia support was prepared by calcining niobic acid (Niobia Products Co.) at 500° C. for two hours. A solution of vanadium triisopropoxide oxide and propanol-2 was thoroughly mixed with the niobia support in a glove box filled with nitrogen, dried at room temperature for 16 hours, further dried at 110–120° C. for 16 hours and calcined at 450° C. for 16 hours. The catalyst was then pelletized, crushed and sieved to obtain catalyst particles sizes between 100 to 200 $\mu$m.

Example 7

Vanadia on Alumina

A vanadium oxide overlayer was deposited on an alumina $(Al_2O_3)$ support (Harshaw, 180 $m^2g^{-1}$) using an organic solution of vanadium triisopropoxide oxide (Alfa, 95–98% purity) and the incipient wetness impregnation. A solution of the vanadium precursor and propanol-2 was thoroughly mixed with the alumina support, in a glove box filled with nitrogen, dried at room temperature for 16 hours, further dried at 110–120° C. for 16 hours and calcined at 500° C. for 16 hours. The catalyst was then pelletized, crushed and sieved to obtain catalyst particles sizes between 100 to 200 μm.

Example 8
Vanadia on Silica

A vanadium oxide overlayer was deposited on an silica ($SiO_2$) support (Cab-O-Sil, 300 $m^2g^{-1}$) using an organic solution of vanadium triisopropoxide oxide (Alfa, 95–98% purity) and the incipient wetness impregnation. A solution of the vanadium precursor and propanol-2 was thoroughly mixed in a glove box filled with nitrogen with the $SiO_2$ support, the wet silica was dried at room temperature for 16 hours, further dried at 110–120° C. for 16 hours and calcined at 500° C. for 16 hours. The catalyst was then pelletized, crushed and sieved to obtain catalyst particles sizes between 100 to 200 μm.

Example 9
Tungsten Oxide on Silica

An aqueous solution of ammonium metatungstate (($NH_4$)$_6H_2W_{12}O_{40}$·$xH_2O$) (Pfaltz & Bauer, 99.9% purity) was deposited as an oxide overlayer onto a silica ($SiO_2$) support (Cab-O-Sil, 300 $m^2g^{-1}$) using the incipient wetness technique. After impregnation, the silica support was dried at room temperature for 16 hours, further dried at 110–120° C. for 16 hours and calcined at 500° C. for 16 hours. The catalyst was then pelletized, crushed and sieved to obtain catalyst particles sizes between 100 to 200 μm.

Example 10
Niobia on Silica

An aqueous solution of niobium oxalate (Niobium Products Co.) was deposited onto a silica ($SiO_2$) support (Cab-O-Sil, 300 $m^2g^{-1}$) using the incipient wetness technique. After impregnation, the silica support was dried at room temperature for 16 hours, further dried at 110–120° C. for 16 hours and calcined at 500° C. for 16 hours. The catalyst was then pelletized, crushed and sieved to obtain catalyst particles sizes between 100 to 200 μm.

Example 11
Titania on Silica

Titanium isopropoxide (Aldrich) in a toluene solution was impregnated onto a silica ($SiO_2$) support (Cab-O-Sil, 300 $m^2g^{-1}$) under a nitrogen blanket to form a titania overlayer using the incipient wetness technique. After impregnation, the wet silica was dried at room temperature for 16 hours, further dried at 110–120° C. for 16 hours and calcined at 500° C. for 16 hours. The catalyst was then pelletized, crushed and sieved to obtain catalyst particles sizes between 100 to 200 μm.

Example 12
Vanadia Tungsten Oxide on Titania

A vanadia and tungsten oxide on titania catalyst was prepared by a two step incipient wetness impregnation method. A vanadium oxide overlayer was deposited first on the $TiO_2$ support using a solution of vanadium triisopropoxide oxide (Alfa, 95–98% purity) and propanol-2 by the incipient wetness impregnation method in a glove box filled with nitrogen. The solution of the vanadium precursor and propanol-2 were thoroughly mixed with the $TiO_2$ (Degussa P25) as the support. The $TiO_2$ support (~10% rutile and ~90% anatase) was prepared by previous calcination in air at 500° C. and cooled to room temperature before impregnation with the vanadium oxide precursor. The support possessed a surface area of ~55 $m^2/g$. After impregnation, the wet $TiO_2$ was dried at room temperature for 16 hours, further dried at 110–120° C. for 16 hours and calcined at 450° C. for 12 hours. Subsequently, an aqueous solution of ammonium metatungstate (($NH_4$)$_6H_2W_{12}O_{40}$·$xH_2O$) was deposited as an oxide overlayer onto the $TiO_2$ support, again using the incipient wetness technique. After impregnation, the wet samples were dried at room temperature for 16 hours, further dried at 110–120° C. for 16 hours and calcined at 500° C. for 16 hours. The catalyst was then pelletized, crushed and sieved to obtain catalyst particles sizes between 100 to 200 μm.

Example 13
Vanadia and Titania on Silica

A vanadia and titania on silica catalyst was prepared by a two step incipient wetness impregnation method. The silica support used for this study was Cabosil EH-5 (380 $m^2/g$). This fluffy material was treated with water in order to condense its volume for easier handling. Then the wet SiO2 was dried at 120° C. and subsequently calcined at 500° C. overnight. The resulting surface area was 332 $m^2/g$. This water pretreatment did not change the dispersion ability of the silica, since an isopropanol pretreated silica also resulted in the same surface area and the same dispersion capacity. A titanium oxide overlayer was deposited first on the silica ($SiO_2$) support under a nitrogen blanket using titanium isopropoxide (Aldrich) in a toluene solution by the incipient wetness impregnation method in a glove box filled with nitrogen. After impregnation, the loaded sample was dried at room temperature for 16 hours, further dried at 110–120° C. for 16 hours and calcined at 500° C. for 4 hours. Subsequently, a solution of vanadium triisopropoxide oxide (Alfa, 95–98% purity) and propanol-2 was impregnated onto the silica ($SiO_2$) support containing titania again using the incipient wetness technique. The solution of the vanadium precursor and propanol-2 was thoroughly mixed with the $SiO_2$ support containing titania. After impregnation, the wet $SiO_2$ was dried at room temperature for 16 hours, further dried at 110–120° C. for 16 hours and calcined at 450° C. for 2 hours. The catalyst was then pelletized, crushed and sieved to obtain catalyst particles sizes between 100 to 200 μm.

The above-synthesized catalysts, as well as one other bulk metal oxide catalyst, were examined for their ability to oxidize methyl mercaptans selectively to formaldehyde generally using the following equipment and methods.

Example 13A

The oxidation reactions were carried out in an isothermal fixed-bed integral mode reactor operating at atmospheric pressure. The methanethiol ($CH_3SH$) diluted in helium, was supplied by Scott Specialty Gases. The reactant gas was further diluted in helium and air (Blue Valley Welding Supply, total hydrocarbons concentration <1 ppm, $H_2O$ concentration <3 ppm) and sent to the reactor through glass tubing connected with Teflon fittings. Flow rates and concentrations were controlled by two mass flow controllers (Brooks 5850 D, 1–100 sccm for helium and Omega FMA-767-V, 0–1 slpm). The lines were heated to 70° C. for the methanethiol oxidation studies to prevent condensation. The total gas flow was maintained between 150 and 200 ml/min. The reactor was kept in a vertical position and made of 6-mm O.D. Pyrex glass. Heating tape was used in conjunction with a feedback temperature controller (Omega CN 9000) to obtain the desired reactor temperature. The catalysts were held at the middle of the reactor tube between a porous glass frit, pore size of 40 to 60 μm, and a glass wool plug. Each catalyst sample was always pretreated by heating at 500° C. for 2 to 3 hours in flowing air, to remove adsorbed water on the catalyst surface prior to initiation of an experiment. The outlet of the reactor was connected to an FTIR cell (Infrared Analysis, Inc; Model #G4-Tin—Ta—Ba—Ag), which was used to analyze the reaction products. The lines between the outlet and the cell were heated to avoid condensation of the products. The flow of reaction products sent to the FTIR cell was controlled by a needle valve (Nupro Company, SS-4BRG).

Analysis of the reaction products was accomplished using a Midac Inc. FTIR, (model #101250, series 2–4). Samples were analyzed in a path gas cell (eared Analysis, Inc; Model #G-4-Tin—Ta—Ba—Ag), which has an effective length of 10 m and a volume of 3.1 L. The spectrometer was controlled by a microcomputer (Sprouse Scientific, model TECH-1000 A) to provide acquisition and manipulation of the spectra: display, subtraction, zoom, etc. The spectra were obtained using 16 scans at a resolution of 0.5 cm$^{-1}$. The FTIR analysis required about 10 minutes.

Methanethiol oxidation was investigated with a variety of supported metal oxide and bulk metal oxide catalysts as follows:

dioxide appeared in small amounts as reaction products; but the formation of CO increased at elevated temperatures. Sulfur dioxide production tracked the formation of formaldehyde.

Examples 15–29

Using substantially the same equipment and procedures as Example 14, a variety of both metal oxide supported catalysts and a bulk metal oxide catalyst were tested for their ability to oxidize methanethiol selectively to formaldehyde. While the majority of the data were obtained at a reaction temperature of 350° C., Examples 21, and 24–26 were run at 400° C., since formaldehyde was not detected in the product using these catalysts at 350° C. The feed gas contained 1150 ppm of methanethiol and was introduced into the reactor at a volumetric flow rate of 150 ml/min. The iron-molybdate catalyst contained iron ($Fe_2O_3$) and molybdenum ($MoO_3$) in a molar ratio (Fe:Mo) of 1.0/2.15 and was obtained from Perstorp. The results of these tests are reported in Table 1.

TABLE 1

| Ex. | Catalyst | Prepn. Ex. | Catalyst Load (mg) | Conversion of $CH_3SH$ (Mole %) | Selectivity (mol %) | | | |
|---|---|---|---|---|---|---|---|---|
| | | | | | HCHO | CO | $CO_2$ | COS |
| 15 | 1.15% $V_2O_5/TiO_2$ | 1 | 10 | 54 | 78 | 11 | 3 | 8 |
| 16 | 1% $V_2O_5/TiO_2$ | 1A | 10 | 48 | 84 | 10 | 4 | 2 |
| 17 | 1% $MoO_3/TiO_2$ | 2 | 100 | 84 | 79 | 12 | 9 | 0 |
| 18 | 1% $CrO_3/TiO_2$ | 3 | 100 | 79 | 81 | 12 | 7 | 0 |
| 19 | 1% $Re_2O_7/TiO_2$ | 4 | 10 | 80 | 76 | 18 | 3 | 2 |
| 20 | $Fe_2(MoO_4)_3$ + $MoO_3$ | — | 100 | 40 | 85 | 10 | 5 | 0 |
| 21 | 1% $V_2O_5/ZrO_2$ | 5 | 10 | 57 | 89 | 8 | 2.6 | 0.4 |
| 22 | 1% $V_2O_5/Nb_2O_5$ | 6 | 20 | 45 | 72 | 21 | 7 | 0 |
| 23 | 1% $V_2O_5/Al_2O_3$ | 7 | 100 | 61 | 37 | 16 | 6 | 41 |
| 24 | 1% $V_2O_5/SiO_2$ | 8 | 100 | 63 | 84 | 9 | 7 | 0 |
| 25 | 1% $WO_3/SiO_2$ | 9 | 100 | 46 | 49 | 11 | 4 | 36 |
| 26 | 2.5% $Nb_2O_5/SiO_2$ | 10 | 100 | 42 | 50 | 13 | 2 | 35 |
| 27 | 10% $TiO_2/SiO_2$ | 11 | 100 | 45 | 65 | 16 | 3 | 16 |
| 28 | 1% $V_2O_5$/7% $WO_3$/$TiO_2$ | 12 | 10 | 52 | 82 | 14 | 4 | 0 |
| 29 | 10% $V_2O_5$/15% $TiO_2/SiO_2$ | 13 | 100 | 71 | 85 | 8 | 7 | 0 |

Example 14

In a series of experiments, a supported oxide catalyst prepared in accordance with Preparation Example 1, comprising about 1% vanadia ($V_2O_5$) on titania ($TiO_2$) catalyst, was contacted with a nitrogen stream containing methanethiol over a wide temperature range in order to optimize the formation of formaldehyde. Mercaptan conversions were measured by both increasing and decreasing the temperature between 200 and 450° C., and no temperature hysteresis was observed. The reaction products of this methanethiol oxidation over the 1% $V_2O_5/TiO_2$ catalyst as a function of temperature is graphically presented in FIG. 1. As illustrated, formaldehyde was found to be the predominant product. In these tests, dimethylthiomethane ($H_2C(SCH_3)_2$) was observed as an intermediate between 200 to 300° C., and dimethyl disulfide ($CH_3S)_2$ was found as an intermediate between 300 to 400° K. Carbon monoxide and carbon It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertains, and these aspects and modifications are within the scope of the invention, which is limited only by the appended claims. In this regard, ways of optimizing the energy utilization in the process of the present invention, to capitalize on the heating and cooling operations desired in operating the process, will be apparent to those skilled in the art.

What is claimed is:

1. A process for producing formaldehyde from methane and hydrogen sulfide by a process comprising the steps of:

a. partially oxidizing said methane under partial oxidation conditions in contact with a partial oxidation catalyst to form a stream containing carbon oxides, b. contacting the carbon oxides stream and hydrogen sulfide with a first catalyst comprising: (i) a metal oxide selected from active oxides from the group consisting of vanadium, niobium, molybdenum, chromium, rhenium, titanium, tungsten, manganese, tantalum, and mixtures thereof, (ii) on a support selected from the group consisting of titania, zirconia, niobia, ceria, tin oxide and mixtures thereof with the proviso that the support and the supported metal are not the same, to convert said carbon oxides and hydrogen sulfide to methyl mercaptans, c. contacting said methyl mercaptans with a second catalyst selected from the group consisting of supported metal oxide oxidation catalysts and bulk metal oxide oxidation catalysts under oxidizing conditions for a time sufficient to convert at least a portion of the methyl mercaptans to formaldehyde and sulfur dioxide, and d. recovering said formaldehyde.

2. A process for producing formaldehyde from a sour natural gas stream containing methane and hydrogen sulfide comprising the steps of:

a. separating $H_2S$ from the sour natural gas, b. partially oxidizing $CH_4$ recovered from the sour natural gas to carbon oxides over a partial oxidation catalyst, c. contacting the carbon oxides and $H_2S$ with a first catalyst comprising (i.) a metal oxide selected from the group consisting of vanadium, niobium, molybdenum, chromium, rhenium, titanium, tungsten, manganese, tantalum, and mixtures thereof, (ii.) on a support selected from the group consisting of titania, zirconia, niobia, ceria, tin oxide and mixtures thereof with the proviso that the support and the supported metal oxide are not the same, under conditions sufficient to convert said carbon oxides and hydrogen sulfide to methyl mercaptans, d. contacting said methyl mercaptans with a second catalyst selected from the group consisting of supported metal oxide oxidation catalysts and bulk metal oxide oxidation catalysts under oxidizing conditions for a time sufficient to convert at least a portion of the methyl mercaptans to formaldehyde and sulfur dioxide, and e. recovering said formaldehyde.

3. The process of claim 1 or 2 wherein the supported metal oxide second catalyst has a metal oxide overlayer of a metal selected from the group consisting of titanium, zirconium, molybdenum, rhenium, vanadium, chromium, tungsten, manganese, niobium, tantalum, and mixtures thereof.

4. The process of claim 3 wherein the supported metal oxide second catalyst has a metal oxide support selected from the group consisting of titania, silica, zirconia, alumina, niobia, magnesia, ceria, lanthanum oxide, tin oxide and mixtures thereof.

5. The process of claim 4 wherein the loading of the metal oxide of vanadium, niobium, molybdenum, chromium, rhenium, titanium, tungsten, manganese, tantalum, and mixtures thereof on the support of the first catalyst ranges between about 0.5 to 30 percent by weight of the first catalyst weight and the metal oxide overlayer of the supported metal oxide second catalyst comprises 0.5 to 35 percent by weight of the supported metal oxide second catalyst.

6. The process of claim 5 wherein the supported metal oxide second catalyst is selected from the group consisting of a vanadia overlayer on a titania support, a molybdenum oxide overlayer on a titania support, a chromium oxide overlayer on a titania support, a rhenium oxide overlayer on a titania support, a vanadia overlayer on a zirconia support, a vanadia overlayer on a niobia support, a vanadia overlayer on an alumina support, a vanadia overlayer on a silica support, a tungsten oxide overlayer on a silica support, a niobia overlayer on a silica support, and a titania overlayer on a silica support.

7. The process of claim 6 wherein the first catalyst and the supported metal oxide second catalyst each comprises a vanadia overlayer on a titania support, wherein the vanadia is present in an amount of 1 to 15% by weight of said catalysts.

8. The process of claim 1 or 2 wherein the bulk metal oxide catalyst is selected from the group consisting of molybdates (Mo), chromates (Cr), vanadates (V), rhenates (Re), titanates (Ti), niobates (Nb), tungstates (W) and mixtures thereof.

9. The process of claim 8 wherein the bulk metal oxide catalyst comprises at least one member selected from the group consisting of $PbV_2O_6$, $NaVO_3$, $Na_3VO_4$, $BiVO_4$, $AlVO_4$, $FeVO_4$, $Mg_3(VO_4)_2$, $Mg_2V_2O_7$, $CeVO_4$, $Zn_3(VO_4)_2$, $CdV_2O_7$, $Zn_2V_2O_7$, $VOPO_4$, $KVO_3$, $Pb_2V_2O_7$, $TlVO_4$, $PbMoO_4$, $CaMoO_4$, $Bi_2Mo_2O_9$, $Bi_3(FeO_4)(MoO_4)_3$, $Na_2MoO_4$, $MnMoO_4$, $Gd_2(MoO_4)_3$, $MgMoO_4$, $CuMoO_4$, $CoMoO_4$, $Fe_2(MoO_4)_3$, $Te_2MoO_7$, $CoMoO_4$, $Al_2(MoO_4)_3$, $Cr_2(MoO_4)_3$, $Na_2Mo_2O_7$, $YNbO_4$, $YbNbO_4$, $LiNbO_3$, $NaNbO_3$, $KNbO_3$, $AlNbO_4$, $K_8Nb_6O_{19}$, $BiNbO_4$, $SbNbO_4$, $NbOPO_4$, $CaNb_2O_6$, $K_4Nb_6O_{17}KCa_2Nb_3O_{10}$, $Li_6WO_6$, $FeWO_4$, $CoWO_4$, $MnWO_4$, $NiWO_4$, $CuWO_4$, $CaWO_4$, $Cs_2WO_4$, $Na_2WO_4$, $BaWO_4$, $Fe_2(WO_4)_3$, $Al_2(WO_4)_3$, $SrWO_4$, $K_2WO_4$, $Na_2W_2O_7$, $Li_2WO_4$, $CsLuW_2O_8$, $BiWO_4$, $Na_2CrO_4$, $Na_2Cr_2O_7$, $Na_2Cr_3O_{10}$, $Na_2Cr_4O_{13}$, $K_2CrO_4$, $K_2Cr_2O_7$, $K_2Cr_3O_{10}$, $K_2Cr_4O_{13}$, $Fe_2(CrO_4)_3$, $CaCrO_4$, $Cs_2CrO_4$, $BiCrO_4$, $NaReO_4$, $Li_6ReO_4$, $Mg(ReO_4)_2$, $NaTiO_4$, $NaTiO_3$, $BaTiO_4$, and $BaTiO_3$.

10. The process of claim 1 or 2 wherein said contacting with the first catalyst is conducted at a temperature between 225° and 450° C.

11. The process of claim 10 wherein said contacting with the second catalyst is conducted at a temperature between 200° and 700° C.

12. The process of claim 6 wherein said contacting with the first catalyst is conducted at a temperature between 250° and 400° C. and said contacting with the second catalyst is conducted at a temperature between 325° and 500° C.

13. The process of claim 12 wherein said gas containing said methyl mercaptan is contacted with said second catalyst such that between $10^{-2}$ and $10^4$ cubic centimeters of methyl mercaptan contacts a gram of catalyst per minute.

14. The process of claim 13 wherein between 0.1 and 100 cubic centimeters of methyl mercaptan contact a gram of catalyst per minute.

15. The process of claim 1 or 2 wherein the methyl mercaptan is selected from $CH_3SH$, $CH_3SCH_3$, $CH_3SSCH_3$ and mixtures thereof.

* * * * *

UNITED STATES PATENT AND TRADEMARK OFFICE
CERTIFICATE OF CORRECTION

PATENT NO. : 6,683,221 B1
DATED : January 27, 2004
INVENTOR(S) : Israel E. Wachs It is certified that error appears in the above-identified patent and that said Letters Patent is hereby corrected as shown below:

Column 20,
Line 33, "$K_4Nb_6O_{17}KCa_2Nb_3O_{10}$" has been replaced with -- $K_4Nb_6O_{17}$, $KCa_2Nb_3O_{10}$ --.

Signed and Sealed this

Fifteenth Day of February, 2005

JON W. DUDAS
*Director of the United States Patent and Trademark Office*